US008926175B2

(12) United States Patent
Wendler

(10) Patent No.: US 8,926,175 B2
(45) Date of Patent: Jan. 6, 2015

(54) MULTIPLE USE TEMPERATURE MONITOR ADAPTER, SYSTEM AND METHOD OF USING SAME

(75) Inventor: Mark Wendler, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 65 days.

(21) Appl. No.: 13/273,814

(22) Filed: Oct. 14, 2011

(65) Prior Publication Data

US 2012/0033706 A1 Feb. 9, 2012

Related U.S. Application Data

(63) Continuation of application No. 12/428,887, filed on Apr. 23, 2009, now Pat. No. 8,057,095.

(51) Int. Cl.
| | |
|---|---|
| *G01K 1/00* | (2006.01) |
| *G01K 1/14* | (2006.01) |
| *G01K 13/00* | (2006.01) |
| *G01K 13/02* | (2006.01) |
| *A61M 1/36* | (2006.01) |

(52) U.S. Cl.
CPC ............... *G01K 1/14* (2013.01); *G01K 13/002* (2013.01); *G01K 13/02* (2013.01); *A61M 1/3666* (2013.01); *A61M 2205/3368* (2013.01); *G01K 2013/026* (2013.01)
USPC ............................ 374/208; 600/549; 374/100

(58) Field of Classification Search
CPC ......... G01K 1/14; G01K 13/002; G01K 1/08; G01K 13/02; G01K 1/143; G01K 7/42; G01K 7/01; G01K 1/16; E03C 2001/0418; F28F 2200/005; G06F 1/206; A61B 5/02416; A61B 5/0261; A61B 3/1233; A61B 5/024; A61B 5/02427; A61B 5/01; A61B 5/015; A61B 5/0008; A61B 5/6853; A61M 1/16; A61M 1/3639; A61M 1/3693; A61M 1/3653; A61M 1/3621; A61M 1/3679; A61M 1/34; A61M 1/3687; A61M 1/36; A61M 1/369; A61M 1/3472; A61M 2202/08; A61M 27/002; A61M 2205/8206; A61M 2001/2696; A61M 2205/12; A61M 2001/303; A61M 2205/331; A61M 2205/3393; A61M 2202/3439; A61M 1/3633; A61M 2001/0218; A61M 1/0209; A61M 1/3496; A61M 2001/3696; A61M 1/1678; A61M 1/30; A61M 2001/302; A61M 2001/306; A61M 2001/308; A61M 1/3681; A61M 2001/3683; A61M 1/3627; A61M 39/223; A61M 1/02; A61M 1/0005; A61M 1/3624; A61M 1/1037; A61M 1/101; A61M 1/0009; A61M 1/0062; A61M 1/0058; A61M 5/44; A61M 2205/366; A61M 2018/00011; A61M 1/1698; A61M 2025/1052; A61M 1/3666; A61M 25/0032; A61M 2001/3632; A61M 1/0001; A61M 2025/0031; A61M 25/007; A61M 2025/0037; A61L 2/0011; A61L 2/0082; A61L 2/001; A61K 35/14; A61K 38/1709; B04B 5/0442; A61F 2007/126
USPC .................. 374/163, 208, 147; 604/283, 905, 604/4.01–6.16, 256, 537, 533; 600/474, 600/549
See application file for complete search history.

(56) References Cited

U.S. PATENT DOCUMENTS

| | | |
|---|---|---|
| 3,383,203 A | 5/1968 | Corbett |
| 4,133,312 A | 1/1979 | Burd |

(Continued)

*Primary Examiner* — Lisa Caputo
*Assistant Examiner* — Janice M Soto

(57) ABSTRACT

An adapter slip configured to be seated in a fluid port, the adapter slip including a lumen, an exterior wall, a shoulder, and a sleeve. The lumen extending along a length of a longitudinal axis, the lumen configured to receive a temperature probe. The exterior wall including a proximal end portion and a distal end portion, wherein the proximal end portion includes a tapered portion tapered at an acute angle with respect to the longitudinal axis. The shoulder extending outward from the exterior wall distal to the tapered portion configured to engage with a distal end of the fluid port. The sleeve configured extend within the lumen and project a predetermined distance beyond the proximal end portion of the exterior wall, the sleeve including a sleeve lumen and a closed proximal end, the sleeve lumen configured to receive at least a temperature sensor of the temperature probe.

8 Claims, 9 Drawing Sheets

(56) References Cited

U.S. PATENT DOCUMENTS

| | | |
|---|---|---|
| 4,187,848 A | 2/1980 | Taylor |
| 4,237,091 A | 12/1980 | Lobdell et al. |
| 4,266,815 A | 5/1981 | Cross |
| 4,294,250 A | 10/1981 | Dennehey |
| 4,369,781 A | 1/1983 | Gilson et al. |
| 4,439,188 A | 3/1984 | Dennehey et al. |
| 4,452,473 A | 6/1984 | Ruschke |
| 4,559,043 A | 12/1985 | Whitehouse et al. |
| 4,639,019 A | 1/1987 | Mittleman |
| 4,642,091 A | 2/1987 | Richmond |
| 4,826,477 A | 5/1989 | Adams |
| 4,995,872 A | 2/1991 | Ferrara |
| 5,047,021 A | 9/1991 | Utterberg |
| 5,057,093 A | 10/1991 | Clegg et al. |
| 5,071,413 A * | 12/1991 | Utterberg ............... 604/533 |
| 5,185,004 A | 2/1993 | Lashinski |
| 5,195,869 A | 3/1993 | Groenhoff |
| 5,209,740 A | 5/1993 | Bryant et al. |
| 5,215,538 A | 6/1993 | Larkin |
| 5,250,038 A | 10/1993 | Melker et al. |
| 5,251,873 A | 10/1993 | Atkinson et al. |
| 5,290,222 A | 3/1994 | Feng et al. |
| 5,295,657 A | 3/1994 | Atkinson |
| 5,295,658 A | 3/1994 | Atkinson et al. |
| 5,306,243 A | 4/1994 | Bonaldo |
| 5,395,352 A | 3/1995 | Penny |
| 5,402,982 A | 4/1995 | Atkinson et al. |
| 5,441,487 A | 8/1995 | Vedder |
| 5,474,536 A | 12/1995 | Bonaldo |
| 5,474,544 A | 12/1995 | Lynn |
| 5,478,331 A | 12/1995 | Heflin et al. |
| 5,501,426 A | 3/1996 | Atkinson et al. |
| 5,507,732 A | 4/1996 | McClure et al. |
| 5,533,708 A | 7/1996 | Atkinson et al. |
| 5,549,651 A | 8/1996 | Lynn |
| 5,601,540 A | 2/1997 | Stevens |
| 5,620,427 A | 4/1997 | Werschmidt et al. |
| 5,676,346 A | 10/1997 | Leinsing |
| 5,685,866 A | 11/1997 | Lopez |
| 5,688,254 A | 11/1997 | Lopez et al. |
| 5,690,612 A | 11/1997 | Lopez et al. |
| 5,694,686 A | 12/1997 | Lopez |
| 5,695,466 A | 12/1997 | Lopez et al. |
| 5,700,248 A | 12/1997 | Lopez |
| 5,735,813 A | 4/1998 | Lewis |
| 5,830,195 A | 11/1998 | Peters et al. |
| 5,871,500 A | 2/1999 | Jepson et al. |
| 5,873,862 A | 2/1999 | Lopez |
| 5,901,942 A | 5/1999 | Lopez |
| 5,928,204 A | 7/1999 | Lopez |
| 5,947,954 A | 9/1999 | Bonaldo |
| 5,957,894 A | 9/1999 | Kerwin et al. |
| 5,957,898 A | 9/1999 | Jepson et al. |
| 5,964,785 A | 10/1999 | Desecki et al. |
| 6,003,553 A | 12/1999 | Wahlberg |
| 6,019,748 A | 2/2000 | Lopez |
| 6,096,022 A | 8/2000 | Laymon et al. |
| 6,113,572 A | 9/2000 | Gailey et al. |
| 6,132,403 A | 10/2000 | Lopez |
| 6,142,446 A | 11/2000 | Leinsing |
| 6,152,913 A | 11/2000 | Feith et al. |
| 6,193,697 B1 | 2/2001 | Jepson et al. |
| 6,217,568 B1 | 4/2001 | Jepson et al. |
| 6,228,073 B1 | 5/2001 | Noone et al. |
| 6,261,282 B1 | 7/2001 | Jepson et al. |
| RE37,357 E | 9/2001 | Lynn |
| 6,319,236 B1 | 11/2001 | Bock |
| 6,325,782 B1 | 12/2001 | Lopez |
| 6,344,033 B1 | 2/2002 | Jepson et al. |
| 6,394,983 B1 | 5/2002 | Mayoral et al. |
| 6,413,250 B1 | 7/2002 | Smith |
| 6,511,472 B1 | 1/2003 | Hayman et al. |
| 6,530,912 B2 | 3/2003 | Crank et al. |
| 6,569,118 B2 | 5/2003 | Pilkington et al. |
| RE38,145 E | 6/2003 | Lynn |
| 6,575,960 B2 | 6/2003 | Becker et al. |
| 6,652,489 B2 | 11/2003 | Trocki et al. |
| 6,669,673 B2 | 12/2003 | Lopez |
| 6,669,681 B2 | 12/2003 | Jepson et al. |
| 6,673,059 B2 | 1/2004 | Guala |
| 6,699,184 B2 | 3/2004 | Felix et al. |
| 6,709,424 B1 | 3/2004 | Knierbein |
| 6,808,521 B1 | 10/2004 | McMichael |
| 6,875,193 B1 | 4/2005 | Bonnette et al. |
| 6,908,459 B2 | 6/2005 | Harding et al. |
| 6,955,660 B2 | 10/2005 | Fisher |
| 7,025,744 B2 | 4/2006 | Utterberg et al. |
| 7,090,658 B2 | 8/2006 | Faries, Jr. et al. |
| 7,101,361 B2 | 9/2006 | Gardeski |
| 7,118,560 B2 | 10/2006 | Bonaldo |
| 7,128,348 B2 | 10/2006 | Kawamura et al. |
| 7,140,592 B2 | 11/2006 | Phillips |
| 7,201,513 B2 * | 4/2007 | Nakabayashi ............... 374/208 |
| 7,241,285 B1 | 7/2007 | Dikeman |
| 7,316,679 B2 | 1/2008 | Bierman |
| 7,329,249 B2 | 2/2008 | Bonaldo |
| 7,350,764 B2 | 4/2008 | Raybuck |
| 7,354,427 B2 | 4/2008 | Fangrow |
| 8,142,073 B2 * | 3/2012 | Clark ............... 374/208 |
| 2007/0032776 A1 | 2/2007 | Skinner et al. |
| 2007/0242728 A1 | 10/2007 | Althofer et al. |
| 2008/0048144 A1 | 2/2008 | Lynn |
| 2009/0268779 A1 * | 10/2009 | Hotta et al. ............... 374/179 |
| 2010/0272148 A1 | 10/2010 | Wendler |

* cited by examiner

MULTIPLE USE TEMPERATURE MONITOR ADAPTER, SYSTEM AND METHOD OF USING SAME

CROSS-REFERENCE TO RELATED APPLICATIONS

This application is a continuation of U.S. application Ser. No. 12/428,887, filed Apr. 23, 2009, the contents of which are hereby incorporated by reference in their entirety.

FIELD

The present invention relates generally to devices, systems and methods for making and using a multiple use temperature monitor adapter.

BACKGROUND

Temperature sensors are utilized in many different forms and in countless situations. While in some circumstances the results generated by the temperature sensor need not be highly accurate, in many applications a relatively high degree of precision is desirable or even essential. Furthermore, while in some applications the positioning of the temperature sensor is a simple matter, in situations involving limitations such as confined or obstructed spaces, positioning a temperature sensor in a desirable location may prove difficult. Thus, for certain situations, relatively accurate temperature sensors may be required that may be positioned with a relatively high degree of precision in order to provide acceptably accurate results without obstructing other activities surrounding the temperature sensor.

One such situation pertains to heart-lung machines. In medical situations where a patient's natural circulatory system is either inoperative or must be bypassed, a heart-lung machine, also referred to as a cardiopulmonary bypass circuit, may oxygenate and circulate the patient's blood in the place of the patient's heart and lungs. In addition to oxygenating the blood, such a machine may maintain circulation to help prevent the formation of blood clots and heat and/or cool the blood by use of a heat exchanger.

As such, it may be important to have an accurate measure of the temperature of the blood both entering and leaving the heat exchanger and/or circuit. At the same time, it may be important to carefully control the position of a temperature sensor probe within the blood flow, as the position of the probe in relation to the blood flow may create regions of reduced flow, which may lead to the formation of blood clots. Temperature sensor probes have been developed that have an adequately accurate temperature sensor for use in heart-lung machines.

But, as noted, temperature sensor probes may be needed both before and after the heat exchanger of the heart-lung machine. This dual location requirement may create issues with engaging the probe with the heart-lung machine. For instance, different manufacturers of components of the heart-lung machine may utilize different engagement mechanisms. Or, in certain circumstances, it may be required to have a relatively more secure fit between the temperature probe and the engagement mechanism, such as in circumstances where the blood is under relatively higher pressure. In addition, the optimal positioning of the temperature sensor may vary among different situations. Moreover, it may be desirable to physically separate a temperature probe from the patient's blood, as the probe may be relatively expensive and non-sterilizeable. As such, multiple adapters have been developed for particular situations involving the use of a temperature probe with heart-lung machines. The different adapters allow for one temperature probe to be utilized with different components and different machines, while physically separating the temperature probe from the patient's blood and positioning the probe properly for accurate and safe temperature readings.

SUMMARY

The use of multiple adapters creates various issues with supply and availability. If a particular adapter is not available at a time in which it is needed, the heart-lung machine may not be useable at all, to the potentially fatal detriment of the patient. Furthermore, it may be more expensive to supply multiple different adapters compared against a single model adapter, as increased adapters may mean greater design efforts and a lack of efficiency of scale.

A multiple-use temperature monitoring adapter has been developed that may interface with multiple different ports or engagement mechanisms. The multiple-use adapter may be utilized in particular with heart-lung machines. By providing a single adapter for the temperature probe which may be used with many different engagement mechanisms on the heart-lung machine the availability of adapters may be enhanced while the cost may be reduced.

In an embodiment, the present invention provides a probe assembly for use with an elongated fluid conduit having a lateral fluid port, the fluid port having a longitudinal axis and a first end proximal the fluid conduit and a second end opposite the first end and having a tapered interior surface at a port taper angle, the port taper angle being acute with respect to the longitudinal axis of the lateral fluid port, the tapered interior surface forming a port lumen, the port lumen being narrower at the first end than at the second end. The assembly includes an adapter slip having a longitudinal axis, a proximal end, a slip lumen and an exterior wall, at least a portion of the exterior wall nearest the proximal end of the adapter slip being tapered at an adapter taper angle, the adapter taper angle is acute with respect to the longitudinal axis of the adapter slip, the exterior wall is narrower at the proximal end of the adapter slip than away from the proximal end of the adapter slip. The adapter taper angle of the exterior wall of the adapter slip is less than the port taper angle of the interior surface of the lateral fluid port. The adapter slip is sized relative to the fluid port such that the exterior wall of the adapter slip provides an interference fit with at least a portion of the interior surface of the fluid port at the proximal end of the adapter slip when the proximal end of the adapter slip is inserted into the fluid port. The adapter slip has an external shoulder, the external shoulder abutting the second end of the fluid port when the proximal end of the adapter slip is inserted into the fluid port, wherein, when the external shoulder abuts the second end of the fluid port. The adapter slip has a sleeve having a closed proximal end, the closed proximal end of the sleeve having a known predetermined position with respect to the proximal end of the adapter slip. A probe is configured to be seated in the slip lumen with a proximate end of the probe being proximate to the closed proximal end of the sleeve.

In another embodiment, the present invention provides a probe assembly for use with an elongated fluid conduit having a lateral fluid port, the fluid port having a longitudinal axis and a first end proximal the fluid conduit and a second end opposite the first end and having a tapered interior surface at a port taper angle, the port taper angle being acute with respect to the longitudinal axis of the lateral fluid port, the tapered interior surface forming a port lumen, the port lumen being narrower at the first end than at the second end. The assembly includes an adapter slip having a longitudinal axis, a proximal end, a slip lumen and an exterior wall, at least a portion of the exterior wall nearest the proximal end of the adapter slip is tapered at an adapter taper angle, the adapter taper angle is acute with respect to the longitudinal axis of the adapter slip, the exterior wall is narrower at the proximal end of the adapter slip than away from the proximal end of the adapter slip. The adapter taper angle of the exterior wall of the adapter slip is less than the port taper angle of the interior surface of the lateral fluid port. The adapter slip is sized relative to the fluid port such that the exterior wall of the adapter slip provides an interference fit with at least a portion of the interior surface of the fluid port at the proximal end of the adapter slip when the proximal end of the adapter slip is inserted into the fluid port. An external shoulder of the adapter slip abuts the second end of the fluid port when the proximal end of the adapter slip is inserted into the fluid port, wherein, when the external shoulder abuts the second end of the fluid port, a location of the proximal end of the adapter slip relative to the first end of the fluid port is determined by a length of the adapter slip from the external shoulder to the proximal end of the adapter slip. A probe is configured to be seated in the slip lumen and project a first predetermined distance beyond proximal end of the adapter slip, the probe having a sensor positioned on a first end of the probe, wherein the sensor projects a second predetermined distance into the fluid conduit, the second predetermined distance is limited by the location of the proximal end of the adapter slip and the first predetermined distance.

The present invention further provides an adapter slip having a longitudinal axis and a proximal end for seating in a lateral fluid port of an elongated fluid conduit, the fluid port having a longitudinal axis and a first end proximal the fluid conduit and a second end opposite the first end and having a tapered interior surface at a port taper angle, the port taper angle being acute with respect to the longitudinal axis of the lateral fluid port, the tapered interior surface forming a port lumen, the port lumen being narrower at the first end than at the second end. The adapter slip includes an interior wall that forms a slip lumen. At least a portion of an exterior wall nearest the proximal end of the adapter slip is tapered at an adapter taper angle, the adapter taper angle being acute with respect to the longitudinal axis of the adapter slip, the exterior wall being narrower at the proximal end of the adapter slip than away from the proximal end of the adapter slip, the adapter taper angle of the exterior wall of the adapter slip being less than the port taper angle of the interior surface of the lateral fluid port. An external shoulder abuts the second end of the fluid port when the proximal end of the adapter slip is inserted into the fluid port. A closed proximal end of an adapter sleeve is mated with the adapter slip and has a known predetermined position with respect to the proximal end of the adapter slip. The adapter slip is sized relative to the fluid port such that the exterior wall of the adapter slip provides an interference fit with at least a portion of the interior surface of the fluid port at the proximal end of the adapter slip when the proximal end of the adapter slip is inserted into the fluid port. In one embodiment, the sleeve is seated in said slip lumen. In another, the adapter slip is molded around said sleeve. In one embodiment, the adapter slip further includes a collar coupled to the adapter slip, the collar circumscribing the adapter slip distal to said external shoulder, the collar being configured to engage an exterior surface of said lateral fluid port. In another embodiment, the adapter slip further includes a rib relative to said exterior wall of said adapter slip, wherein said rib provides at least partial interference with at least a portion of said interior surface of said lateral fluid port when said proximal end of said adapter slip is inserted into said fluid port; for example, the rib can form a seal with the interior surface of the lateral fluid port when the proximal end of the adapter slip is inserted into the fluid port. In one example, the slip adapter, is affixed to the lateral fluid port using an adhesive, e.g., positioned distal of the rib, when the proximal end of the adapter slip is inserted into the fluid port. In another embodiment of the adapter slip, the interference between the interior surface of the lateral fluid port and the external surface of the adapter slip forms a seal when the proximal end of the adapter slip is inserted into the fluid port. In one embodiment, the interference occurs only between a portion of the adapter slip and lateral fluid port when the proximal end of the adapter slip is inserted into the fluid port.

The present invention further provides an adapter slip having a longitudinal axis and a proximal end for seating in a lateral fluid port of an elongated fluid conduit, the fluid port having a longitudinal axis and a first end proximal the fluid conduit and a second end opposite the first end and having a tapered interior surface at a port taper angle, the port taper angle being acute with respect to the longitudinal axis of the lateral fluid port, the tapered interior surface forming a port lumen, the port lumen being narrower at the first end than at the second end. The adapter slip includes an interior wall that forms a slip lumen. At least a portion of an exterior wall nearest the proximal end of the adapter slip is tapered at an adapter taper angle, the adapter taper angle being acute with respect to the longitudinal axis of the adapter slip, the exterior wall being narrower at the proximal end of the adapter slip than away from the proximal end of the adapter slip, the adapter taper angle of the exterior wall of the adapter slip being less than the port taper angle of the interior surface of the lateral fluid port. An external shoulder abuts the second end of the fluid port when the proximal end of the adapter slip is inserted into the fluid port with a location of the proximal end of the adapter slip relative to the first end of the fluid port being determined by a length of the adapter slip from the external shoulder to the proximal end of the adapter slip. The adapter slip is sized relative to the fluid port such that the exterior wall of the adapter slip provides an interference fit with at least a portion of the interior surface of the fluid port at the proximal end of the adapter slip when the proximal end of the adapter slip is inserted into the fluid port. In one embodiment, a collar is coupled to the adapter slip, which circumscribes the adapter slip distal to the external shoulder, the collar being configured to engage an exterior surface of the lateral fluid port. In another embodiment, a rib relative to the exterior wall of the adapter slip provides at least partial interference with at least a portion of the interior surface of the lateral fluid port when the proximal end of the adapter slip is inserted into the fluid port. For example, in one embodiment, the rib forms a seal with the interior surface of the lateral fluid port when the proximal end of the adapter slip is inserted into the fluid port. The slip adapter, in one embodiment, is affixed to the lateral fluid port using an adhesive when the proximal end of the adapter slip is inserted into the fluid port. In another embodiment, the adhesive is positioned distal of the rib. In addition, in another embodiment, the interference between the interior surface of the lateral fluid port and the external surface of the adapter slip forms a seal when the proximal end of the adapter slip is inserted into the fluid port. In another embodiment, the interference occurs only between a portion of the adapter slip and lateral fluid port when the proximal end of the adapter slip is inserted into the fluid port.

The present invention further provides an adapter slip having a longitudinal axis and a proximal end for seating in a lateral fluid port of an elongated fluid conduit, the fluid port having a longitudinal axis and a first end proximal the fluid conduit and a second end opposite the first end and having a tapered interior surface at a port taper angle, the port taper angle being acute with respect to the longitudinal axis of the lateral fluid port, the tapered interior surface forming a port lumen, the port lumen being narrower at the first end than at the second end. An interior wall forms a slip lumen. At least a portion of the exterior wall nearest the proximal end of the adapter slip is tapered at an adapter taper angle, the adapter taper angle being acute with respect to the longitudinal axis of the adapter slip, the exterior wall being narrower at the proximal end of the adapter slip than away from the proximal end of the adapter slip, the adapter taper angle of the exterior wall of the adapter slip being less than the port taper angle of the interior surface of the lateral fluid port. An abuts the second end of the fluid port when the proximal end of the adapter slip is inserted into the fluid port, wherein with the closed proximal end of a sleeve having a known predetermined position with respect to the proximal end of the adapter slip. The adapter slip is sized relative to the fluid port such that the exterior wall of the adapter slip provides an interference fit with at least a portion of the interior surface of the fluid port at the proximal end of the adapter slip when the proximal end of the adapter slip is inserted into the fluid port. A rib relative to the exterior wall of the adapter slip provides at least partial interference with at least a portion of the interior surface of the lateral fluid port when the proximal end of the adapter slip is inserted into the fluid port. A collar is coupled to the adapter slip, which circumscribes the adapter slip distal to the external shoulder, configured to engage an exterior surface of a first particular one of the lateral fluid port. The slip adapter is adapted to be affixed to a second particular one of the lateral fluid port using an adhesive when the proximal end of the adapter slip is inserted into the fluid port. The interference between the interior surface of the lateral fluid port and the external surface of the adapter slip is adapted to form a seal when the proximal end of the adapter slip is inserted into a third particular one of the fluid port. For example, in one embodiment the sleeve is seated in the slip lumen. In another embodiment, the adapter slip is molded around the sleeve. In another embodiment, the rib of the adapter slip forms a seal with the interior surface of the lateral fluid port when the proximal end of the adapter slip is inserted into the fluid port. For example, adhesive is positioned distal of the rib. In another embodiment, the interference occurs only between a portion of the adapter slip and lateral fluid port when the proximal end of the adapter slip is inserted into the fluid port.

The present invention further provides an adapter slip having a longitudinal axis and a proximal end for seating in a lateral fluid port of an elongated fluid conduit, the fluid port having a longitudinal axis and a first end proximal the fluid conduit and a second end opposite the first end and having a tapered interior surface at a port taper angle, the port taper angle being acute with respect to the longitudinal axis of the lateral fluid port, the tapered interior surface forming a port lumen, the port lumen being narrower at the first end than at the second end. The adapter slip has a slip lumen and an exterior wall with at least a portion of the exterior wall nearest the proximal end of the adapter slip being tapered at an adapter taper angle, the adapter taper angle being acute with respect to the longitudinal axis of the adapter slip, the exterior wall being narrower at the proximal end of the adapter slip than away from the proximal end of the adapter slip, the adapter taper angle of the exterior wall of the adapter slip being less than the port taper angle of the interior surface of the lateral fluid port. An external shoulder abuts the second end of the fluid port when the proximal end of the adapter slip is inserted into the fluid port, wherein with a location of the proximal end of the adapter slip relative to the first end of the fluid port being determined by a length of the adapter slip from the external shoulder to the proximal end of the adapter slip. The adapter slip is sized relative to the fluid port such that the exterior wall of the adapter slip provides an interference fit with at least a portion of the interior surface of the fluid port at the proximal end of the adapter slip when the proximal end of the adapter slip is inserted into the fluid port. A rib relative to the exterior wall of the adapter slip provides at least partial interference with at least a portion of the interior surface of the lateral fluid port when the proximal end of the adapter slip is inserted into the fluid port. A collar coupled to the adapter slip, which circumscribes the adapter slip distal to the external shoulder, the collar being configured to engage an exterior surface of a first particular one of the lateral fluid port. The slip adapter is adapted to be affixed to a second particular one of the lateral fluid port using an adhesive when the proximal end of the adapter slip is inserted into the fluid port. The interference between the interior surface of the lateral fluid port and the external surface of the adapter slip is adapted to form a seal when the proximal end of the adapter slip is inserted into a third particular one of the fluid port.

In an embodiment, the rib forms a seal with the interior surface of the lateral fluid port when the proximal end of the adapter slip is inserted into the fluid port.

In an embodiment, the adhesive is positioned distal of the rib.

In an embodiment, the interference occurs only between a portion of the adapter slip and lateral fluid port when the proximal end of the adapter slip is inserted into the fluid port.

DRAWINGS

DESCRIPTION

It is often advantageous to know and regulate the temperature of the blood that is being oxygenated and circulated by a heart-lung machine. In many heart-lung machines multiple ports are provided into which temperature probes may be inserted to monitor the temperature of the blood. However, the ports on any given heart-lung machine, or among different heart-lung machines, may not be common, i.e., such ports may have differing configurations. In addition, it may be desirable to physically insulate, i.e., separate, the probe from the patient's blood should the probe be non-sterilizeable or, perhaps, be too expensive to be reasonably disposable.

In order to allow a single temperature probe to be used with different ports or engagement mechanisms on a single heart-lung machine or between and among different heart-lung machines, a multiple-use temperature monitor adapter has been developed. In an embodiment, the adapter may be configured to allow the temperature probe to generate accurate measurements in two or more different temperature ports in heart-lung machines. The adapter may also physically separate the temperature probe from the blood of the patient to allow the temperature probe to be reused in a different adapter without having to sterilize the probe.

Figure 1:
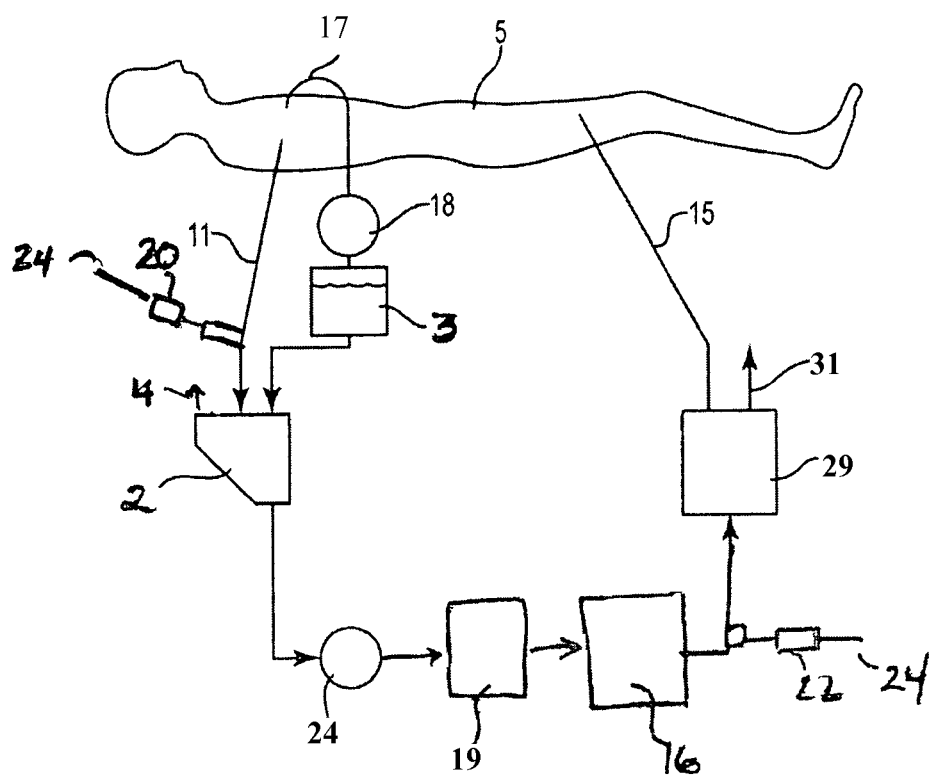
FIG. 1 is an illustration of a patient being aided by a heart-lung machine.

FIG. 1 depicts a patient 5 being aided by heart-lung machine. Briefly, the machine generally draws blood of a patient 5 during a cardiovascular procedure through a venous line 11, oxygenates the blood, and returns the oxygenated blood to the patient 5 through an arterial line 15. Venous blood drawn from the patient through line 11 is discharged into a venous reservoir 2. Cardiotomy blood and surgical field debris are aspirated by a suction device 17 and pumped by pump 18 into a cardiotomy reservoir 3. Once defoamed and defiltered, the cardiotomy blood is also discharged into venous reservoir 2. Alternatively, the function of the cardiotomy reservoir 3 may be integrated into the venous reservoir 2. In the venous reservoir 2, air entrapped in the venous blood rises to the surface of the blood and is vented to the atmosphere through a purge line 4. Blood from patient 5 is directed to flow through inlet fluid port 20 and into venous reservoir 2, then to heat exchanger 19 that maintains the temperature of the blood, then to oxygenator 16 that oxygenates the blood, and then through outlet fluid port 22. Oxygenated and temperature-controlled blood is collected after moving out of the oxygenator 16 and preferably flows to an arterial filter 29 and then into the arterial line 15. The arterial filter 29 preferably traps air bubbles in the blood that are larger than about 20-40 micrometers where the bubbles can be removed through a purge line 31. In order to help control the temperature of the blood, inlet fluid port 20 and outlet fluid port 22 allow for the introduction of temperature probe 24 into the blood flow. In an embodiment, inlet fluid port 20 is a female luer lock consistent with the ISO 594/1-1986 standard. In another embodiment, outlet fluid port 22 is configured to engage temperature probe 24 or an adapter for temperature probe 24 with an adhesive seal. In an alternative embodiment, outlet fluid port 22 is configured with a screw-fit engagement mechanism. Other affixation methods for outlet fluid port 22 are contemplated. The circuit shown in FIG. 1 is exemplary, and it should be understood that the temperature probe 24 may be incorporated into any suitable position along the cardiopulmonary bypass circuit or other suitable extracorporeal system. For example, temperature probe 24 may be used to monitor the temperature at the inlet to the venous reservoir and/or outlet of the oxygenator, as shown, or with alternative components in the circuit, or any combination thereof.

Figure 2:
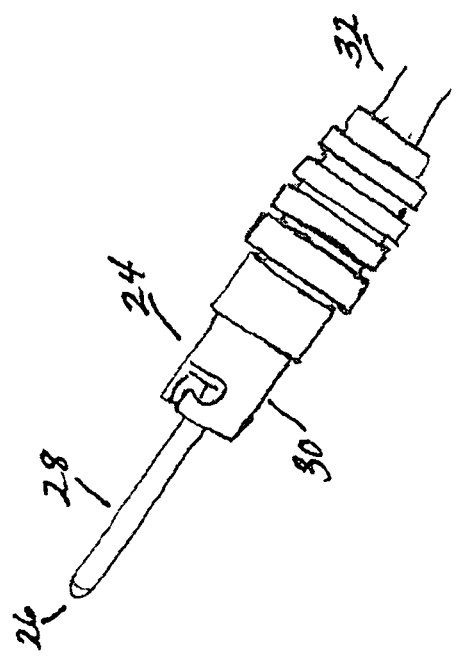
FIG. 2 is an illustration of a temperature probe intended for use with the heart-lung-machine of FIG. 1.

FIG. 2 depicts temperature probe 24 that may be used in conjunction with a fluid port, such as inlet fluid port 20 and/or outlet fluid port 22 of the heart-lung machine shown in FIG. 1. Temperature sensor 26 is positioned at the end of extender 28 to allow temperature sensor 26 to be positioned into relatively narrow conduits and ports. Locking mechanism 30 allows temperature probe 24 to be securely engaged with an adapter or port. Wire 32 is coupled to sensor 26 and transmits data from sensor 26 to a destination for ultimate use. In some embodiments, temperature probe 24 can be sterilized.

Figure 3:
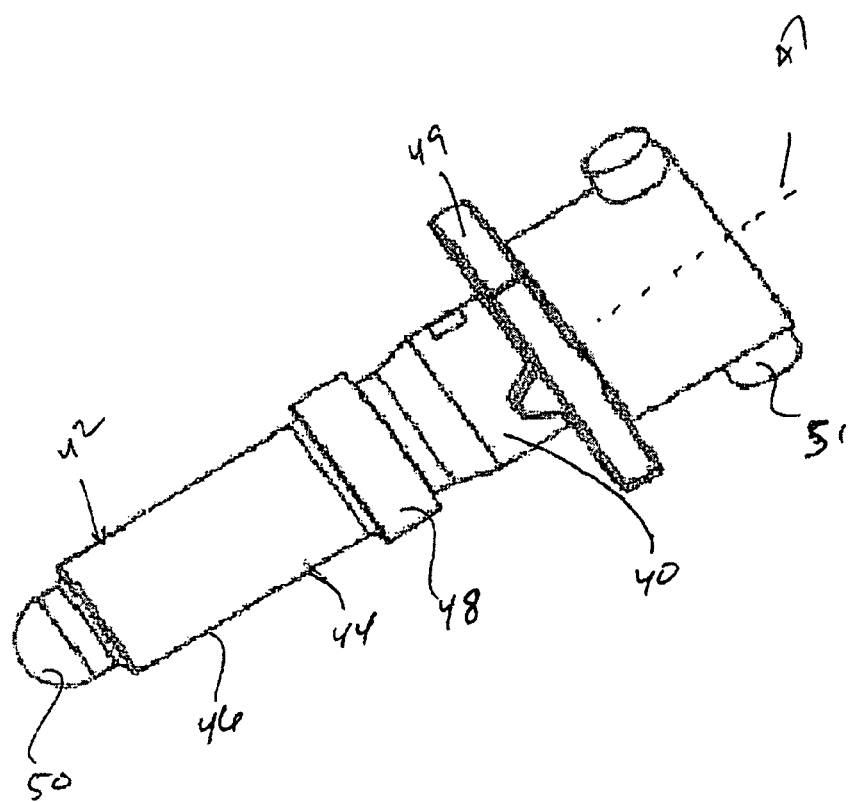
FIG. 3 illustrates a multiple-use adapter slip intended for use with the heart-lung machine of FIG. 1

FIG. 3 shows a multiple-use adapter slip 40 configured to receive temperature probe 24 and itself be seated in inlet fluid port 20 and/or outlet fluid port 22. Proximal end 42 of adapter slip 40 has exterior wall 44, a portion of which is tapered portion 46. Tapered portion 46 is tapered at an acute angle with respect to longitudinal axis 47 of adapter slip 40 in a manner which may be consistent with a female member of a luer lock. Shoulder 48 may provide an engagement stop with a distal end of inlet fluid port 20 and outlet fluid port 22, controlling, at least in part, the depth of penetration of adapter slip within inlet fluid port 20 and outlet fluid port 22, as well as within venous line 11 and arterial line 15. Ring stop 49 may provide engagement with collar 60 (illustrated in FIGS. 5a and 5b). Sleeve 50 may be seated within adapter slip 40. Locking port 51 may be configured to engage with locking mechanism 30 of temperature probe 24. When locking mechanism 30 is engaged with locking port 51, temperature probe 24 and adapter slip 40 may be adequately securely coupled for medical applications.

In an embodiment, proximal end 42 is made from a thermoplastic, such as acrylonitrile butadiene styrene. In alternative embodiments, materials that are relatively rigid and non-porous are utilized. In further embodiments, the material of proximal end 42 is utilized everywhere on adapter slip 40 except for sleeve 50. In various embodiments, proximal end 42 may be formed so that no seam exists in proximal end 42. In alternative embodiments, a seam may be present, in some such embodiments the seam may be reduced in size by an abrasive or similar treatment.

In an embodiment, sleeve 50 is metallic, for example, brass plated with nickle. In an alternative embodiment, sleeve 50 is made from brass plated with nickel plated with gold. In such an embodiment, the brass is 260 brass, the nickel is electroless nickel per the AMS-2404AS standard and is 0.00005 to 0.0001 inches thick, and the gold is plated over the nickel per the SAE AMS 2422D and SATM B488 01, Type II, Grade C standard, and is 0.00001 to 0.00002 inches thick.

Figure 4:
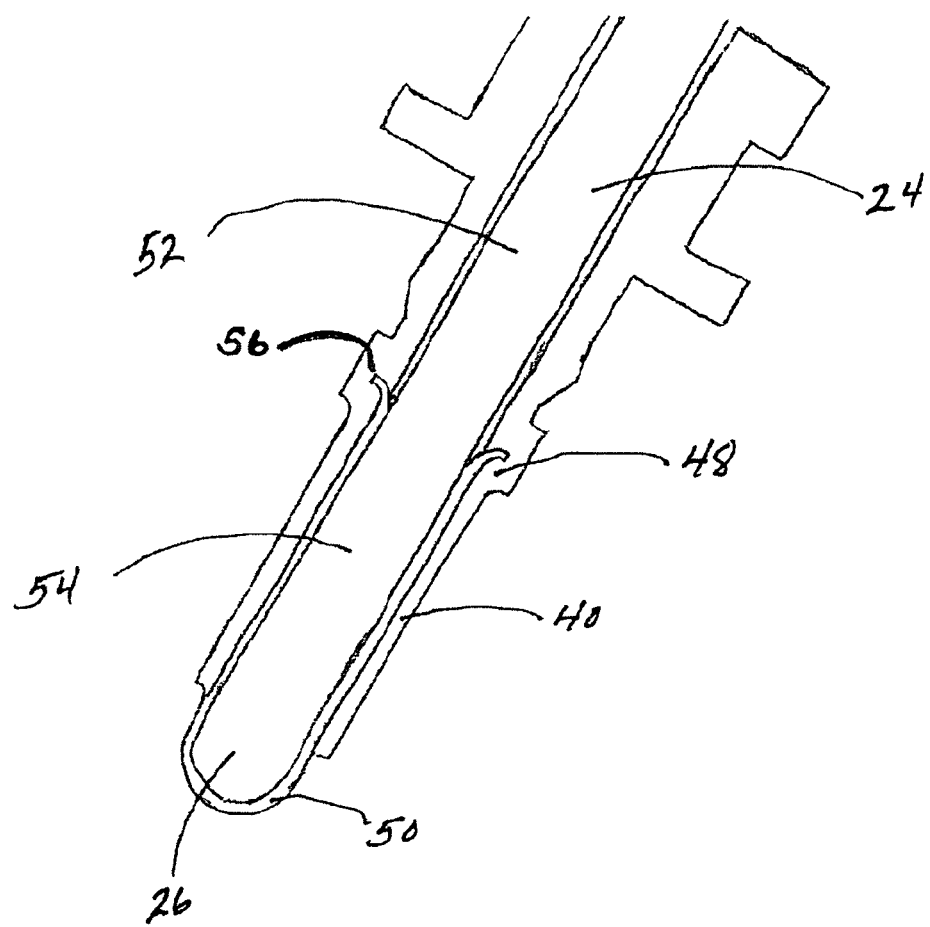
FIG. 4 is a cut-away drawing of the adapter slip of FIG. 3.

FIG. 4 shows a cut-away drawing of adapter slip 40. The interior of adapter slip 40 is hollow slip lumen 52 in which sleeve 50 is seated. As illustrated, sleeve 50 has sleeve lumen 54 which is configured with a sufficiently wide diameter to allow sensor 26 and extender 28 of temperature probe 24 to be seated in sleeve lumen 54. In alternative embodiments, sleeve 50 does not extend back to shoulder 48. In such embodiments, sleeve lumen 54 may be relatively shorter than illustrated, or not exist at all. In such an embodiment, temperature probe 24 may be seated in slip lumen 52 and contact sleeve 50 with sensor 26 and no other portion of temperature probe 24.

In the illustrated embodiment, sleeve 50 is seated in lumen 52, with base 56 of sleeve 50 proximate the material making up shoulder 48. In the illustrated embodiment, a thermoplastic portion of adapter slip 40 is injection molded around sleeve 50. The material of the adapter slip 40 may shrink as it cools, which may secure sleeve 50 in the plastic and provide a watertight seal. The watertight seal may prevent blood and other biological material from coming into contact with temperature probe 24.

Figure 5B:
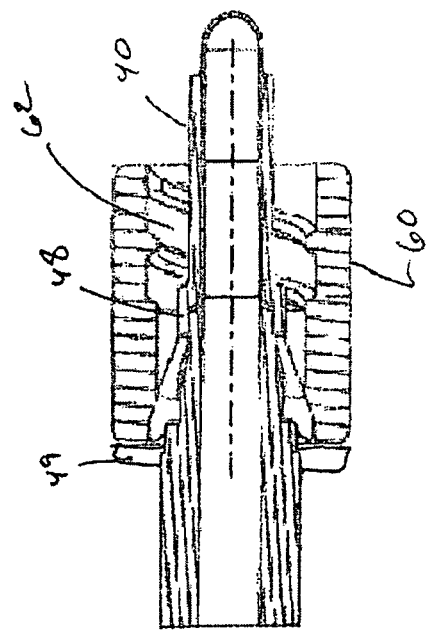
FIG. 5a and FIG. 5b are illustrations of the adapter slip of FIG. 3 with a collar attached.
Figure 5A:
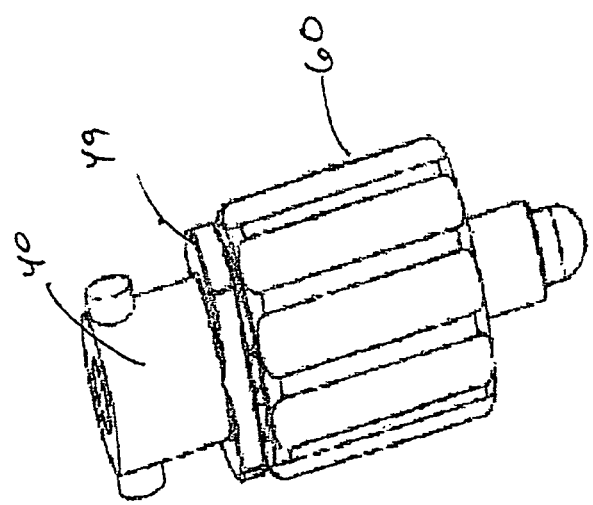

FIGS. 5a and 5b illustrate adapter slip 40 with collar 60 attached. As shown in the cutaway of FIG. 5b, collar 60 may engage with adapter slip 40 by snap-fit engagement distal of shoulder 48 and proximate ring stop 49. Alternative engagement methods are also envisioned, including adhesive engagement and screw-fit engagement. Helical grooves 62 of collar provide a screw-fit receptor for inlet port 20 or outlet port 22, which may be configured with a male screw-fit port. By screwing adapter slip 40 with collar 60 attached into engagement with inlet port 20 or outlet port 22, a fluid-tight lock may be attained that may be relatively more secure against dislodgement from pressure internal to portions of a heart lung machine than a luer lock. As such, it may be advantageous to utilize collar 60 when internal pressure is relatively high and a luer lock when internal pressure is relatively low.

Figure 6A:
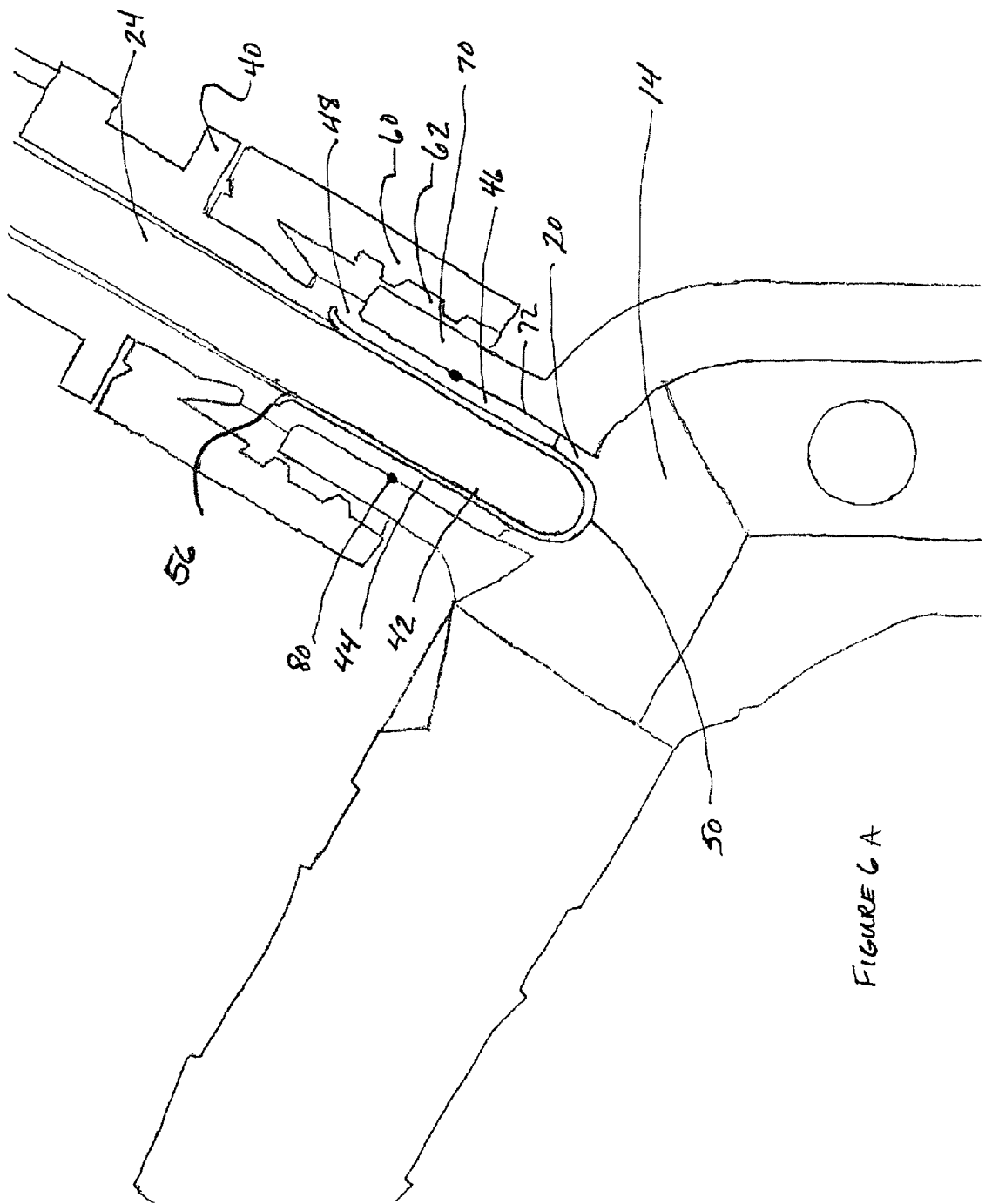
FIG. 6a is a cutaway illustration of the adapter slip of FIG. 3 with a temperature probe and collar positioned in an inlet port.
Figure 6B:
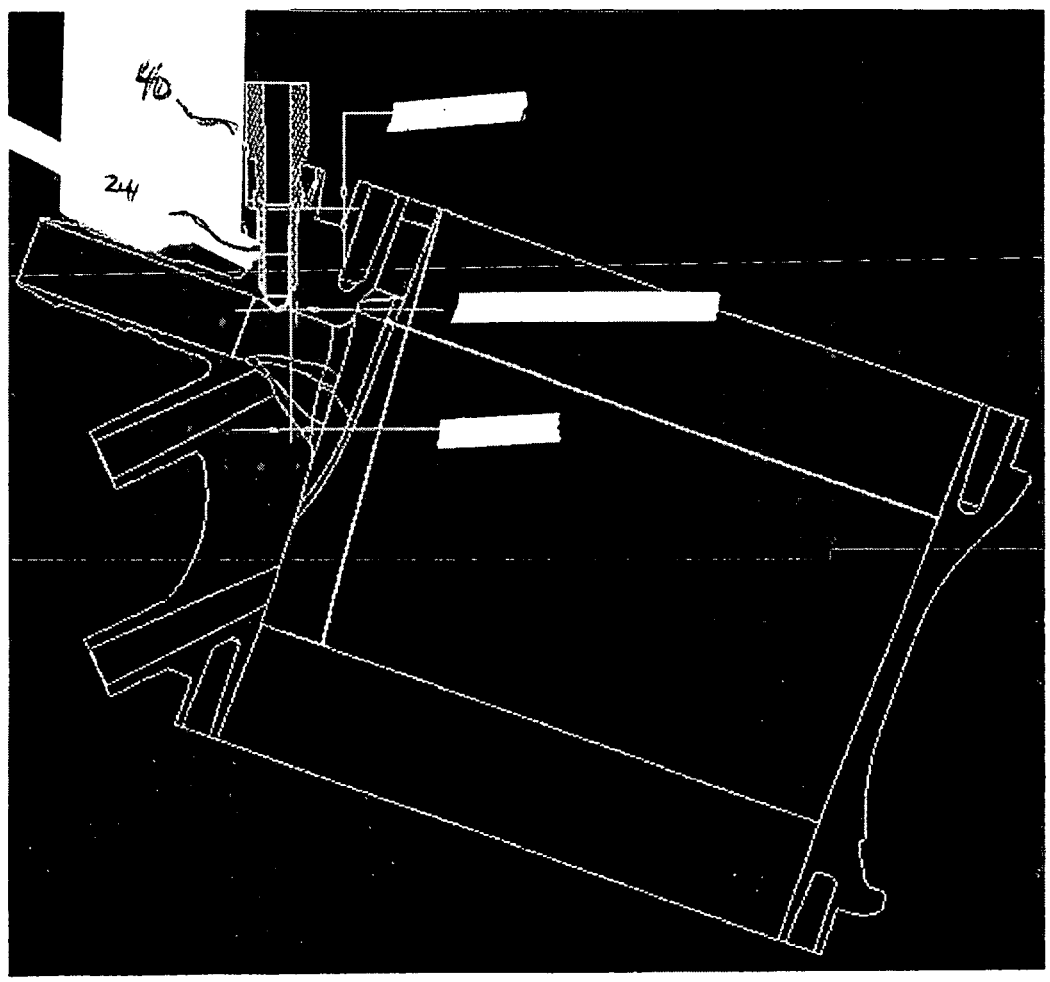
FIG. 6b is an illustration of the adapter slip of FIG. 3 with a temperature probe without a collar.

FIG. 6 is a cutaway illustration of adapter slip 40 with temperature probe 24 and collar 60 positioned in inlet port 20. As illustrated, inlet port 20 is not configured with screw-fit grooves to mate with grooves 62 of collar 60. However, in alternative embodiments, such grooves may be available.

As illustrated, shoulder 48 engages with end 70 of inlet port 20 and may combine with the luer fit of adapter slip 40 with inlet port 20 to establish the distance into venous line 11 which sleeve 50 extends. To create the luer fit between adapter slip 40 and inlet port 20, in an embodiment, the taper angle 90 (FIG. 7) of tapered portion 46 of adapter slip 40 may be consistent with the ISO 594/1-1986 standard. In various embodiments the taper angle may exceed the specification for a luer taper consistent with the ISO 594/1-1986 standard. Collar 48 and the luer fit created by taper portion 46 and interior surface 72 of inlet port 20 may, alone or in combination, establish the distance sleeve 50 extends into venous line 11.

As illustrated, an adhesive may be applied such that the adhesive forms a bond between proximal end 42 of adapter slip 40 and inlet port 20 between shoulder 48 and tapered portion 46. In alternative embodiments, adhesive may be in tapered portion 46 as well, in both tapered portion 46 and the space between tapered portion 46 and shoulder 48, and in alternative portions of exterior wall 44. The adhesive may provide affixing qualities, securing adapter slip 40 to inlet port 20 more firmly than may be possible with a luer lock by itself. The adhesive may also provide fluid isolation, preventing, at least in part, fluid from seeping around adapter slip 40. Such fluid isolation provided by adhesive may be unnecessary in many embodiments, with the luer lock between adapter slip 40 and inlet port 20 providing adequate fluid isolation.

Adapter slip 40 may further incorporate circumferential rib 80 on or proximate tapered portion 46. Rib 80 may prevent or reduce the amount of applied adhesive penetrating into inlet port 20 when the adhesive is applied between rib 80 and shoulder 48. In addition, rib 80 may increase the security of the luer lock and the fluid isolation without incorporating adhesive, thereby potentially obviating a need for adhesive.

Figure 7:
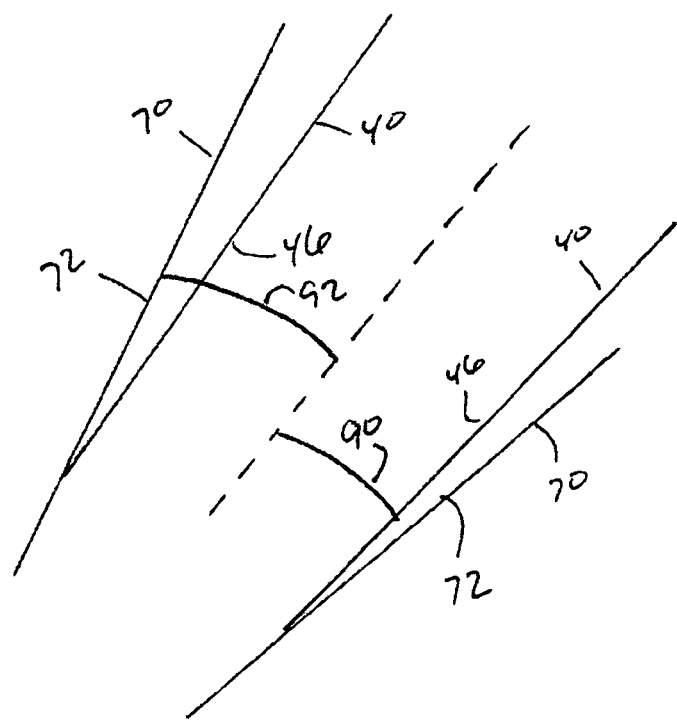
FIG. 7 is an exaggerated illustration of the adapter slip of FIG. 3 with the inlet port of FIG. 6.

FIG. 7 shows an exemplary relationship between tapered portion 46 of adapter slip 40 and interior surface 72 of inlet port 20, the relationships and angles exaggerated for illustrative purposes. Tapered portion 46 forms taper angle 90 with respect to longitudinal axis 47. Interior surface 72 forms port taper angle 92 with respect to longitudinal axis 47. As noted in the discussion of FIG. 6, taper angle 90 may be consistent with, or exceed, the specification of the ISO 594/1-1986 standard. In an embodiment, port taper angle 92 may be consistent with the ISO 594/1-1986 standard. In alternative embodiments, taper angle 90 and port taper angle 92 may be varied as appropriate to alter a sealing qualify of the luer lock created between tapered portion 46 and interior surface 72, to modify engagement of shoulder 48 with end 70, or for other purposes as conditions may warrant.

Figure 8:
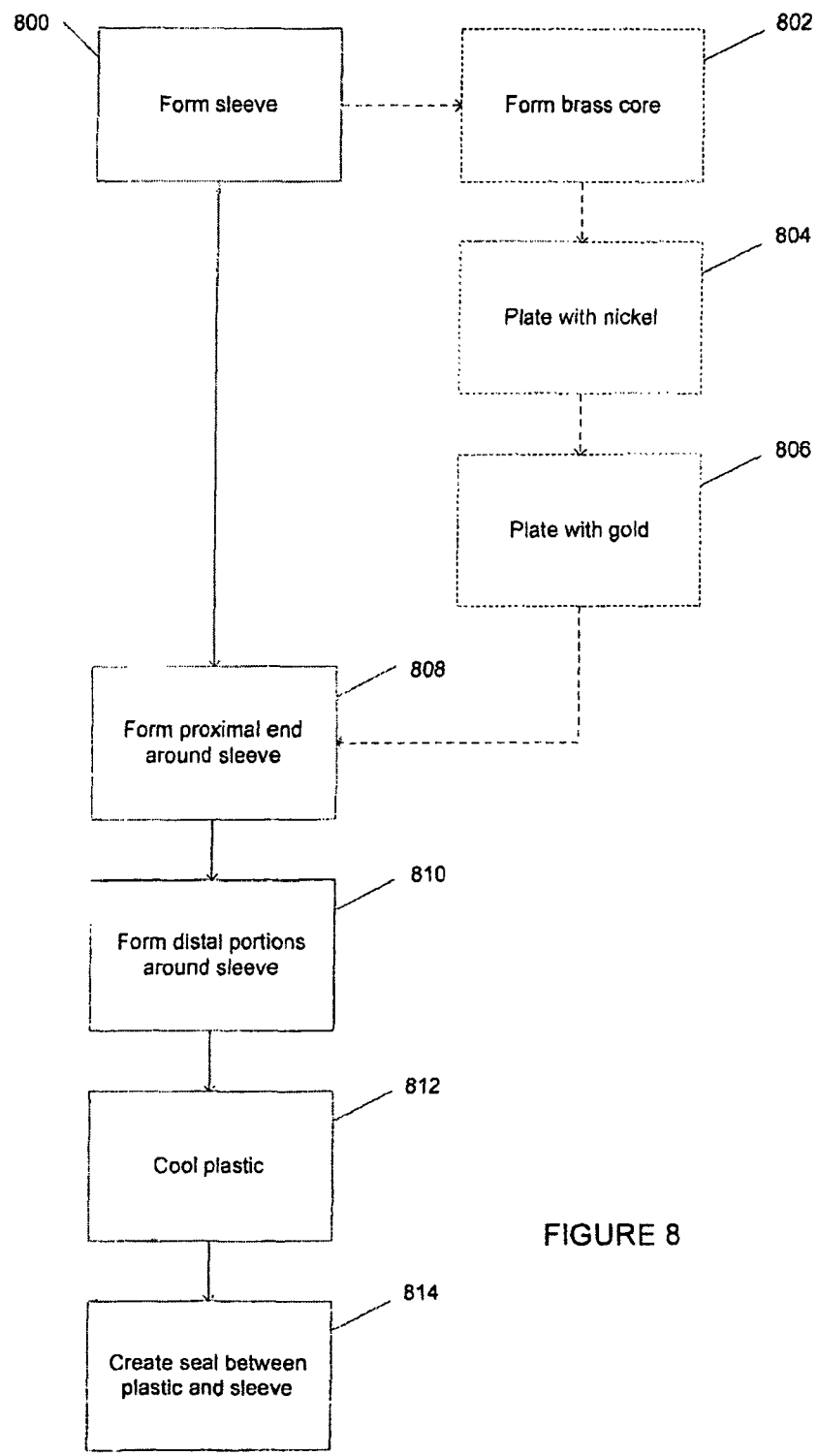
FIG. 8 is a flowchart of a method for the making of an adapter slip.

FIG. 8 is a flowchart for the making of adapter slip 40. Sleeve 50 is formed (800). In an embodiment, the formation of sleeve 50 includes forming (802) a brass core, then plating (804) the brass core with nickel and plating (806) the nickel with gold. Proximal end 42 may be formed (808) around sleeve 50 such that no seam is present in proximal end, and plastic portions of adapter slip may be formed (810) distal of proximal end 42 and around sleeve 50. As proximal end 42 and the rest of adapter slip 40 cool (812) the material may shrink, creating (814) a seal between the metal of sleeve 50 and the plastic portions.

In an embodiment, a seamless proximal end 42 may be formed by creating a generally cylindrical mold for proximal end 42, and by creating half-cylinder molds for portions distal of proximal end 42. When joined to create adapter slip 40, the cylindrical mold of proximal end 42 may prevent any seams in proximal end 42, with the seams occurring in the junction between proximal end 42 and the rest of adapter slip 40, along with seams running longitudinally up opposite sides of the rest of adapter slip 40. In alternative embodiments, molds incorporating only one or two pieces may be utilized.

Thus, embodiments of the devices, system and methods of a multiple use temperature monitor adapter are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A probe assembly configured to removably attach to multiple different fluid ports of a heart-lung machine to measure temperature of blood flow, the probe assembly, comprising:
   a temperature probe including an extender, a temperature sensor positioned at a proximal end of the extender, and a wire coupled to the temperature sensor configured to transmit data from the sensor related to the temperature of blood flow in the heart-lung machine; and
   an adapter slip configured to receive the temperature probe and configured to be seated in each of the multiple different fluid ports of the heart-lung machine, the adapter slip including a proximal end, an external shoulder, a longitudinal axis, and a lumen;
   wherein the external shoulder is configured to provide an engagement stop with a distal end of each of the multiple different fluid ports; and
   wherein the proximal end of the adapter slip has a tapered portion tapered at an acute angle with respect to the longitudinal axis such that at least a portion of the tapered portion provides an interference fit with an interior surface of each of the multiple different fluid ports.

2. The probe assembly of claim 1, further comprising a sleeve seated within the lumen of the adapter slip, the sleeve comprising:
   a sleeve lumen having an interior diameter configured to allow insertion of the temperature probe;
   a closed proximal end positionable at a predetermined distance proximal to the proximal end of the adapter slip.

3. The probe assembly of claim 1, wherein the adapter slip further comprises a locking port configured to engage with a locking mechanism of the temperature probe.

4. The probe assembly of claim 1, further comprising a collar coupled to the adapter slip distal to the external shoulder and apart from a fluid port of the multiple different fluid ports, the collar configured to selectively engage with an exterior surface of the fluid port.

5. The probe assembly of claim 4, wherein the collar includes helical grooves configured to provide a screw-fit receptor for the fluid port.

6. The probe assembly of claim 4, wherein the adapter slip further comprises a ring stop configured for engagement with the collar.

7. The probe assembly of claim 1, further comprising adhesive applied between an exterior wall at the proximal end of the adapter slip and the interior surface of the fluid port.

8. The probe assembly of claim 1, wherein the adapter slip further comprises an external circumferential rib configured to provide at least partial interference and seal with the interior surface of the fluid port.

* * * * *